United States Patent
Guo et al.

(10) Patent No.: US 10,364,184 B2
(45) Date of Patent: Jul. 30, 2019

(54) MANUFACTURING METHOD OF BIG-MODEL LOW-PERMEABILITY MICROCRACK CORE

(71) Applicant: SOUTHWEST PETROLEUM UNIVERSITY, Chengdu (CN)

(72) Inventors: Ping Guo, Chengdu (CN); Shuai Wu, Chengdu (CN); Yijian Chen, Chengdu (CN); Huimin Zhang, Chengdu (CN); Wanbo Zhang, Chengdu (CN); Yuhong Du, Chengdu (CN); Zhouhua Wang, Chengdu (CN); Jianfen Du, Chengdu (CN); Yisheng Hu, Chengdu (CN); Huang Liu, Chengdu (CN); Hongmei Ren, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 24 days.

(21) Appl. No.: 15/749,780

(22) PCT Filed: Feb. 14, 2017

(86) PCT No.: PCT/CN2017/073489
§ 371 (c)(1),
(2) Date: Feb. 2, 2018

(87) PCT Pub. No.: WO2018/141118
PCT Pub. Date: Aug. 9, 2018

(65) Prior Publication Data
US 2019/0002344 A1    Jan. 3, 2019

(30) Foreign Application Priority Data

Feb. 6, 2017 (CN) .......................... 2017 1 0065729

(51) Int. Cl.
| | |
|---|---|
| C04B 20/10 | (2006.01) |
| C04B 28/04 | (2006.01) |
| C04B 14/04 | (2006.01) |
| C04B 40/00 | (2006.01) |
| G01N 1/28 | (2006.01) |
| C04B 14/06 | (2006.01) |
| B28B 7/38 | (2006.01) |
| C04B 111/00 | (2006.01) |
| C09K 8/46 | (2006.01) |

(52) U.S. Cl.
CPC .......... *C04B 20/1025* (2013.01); *B28B 7/384* (2013.01); *C04B 14/04* (2013.01); *C04B 14/06* (2013.01); *C04B 28/04* (2013.01); *C04B 40/0067* (2013.01); *G01N 1/286* (2013.01); *C04B 2111/00991* (2013.01); *C09K 8/46* (2013.01); *G01N 2001/2866* (2013.01); *G01N 2001/2893* (2013.01)

(58) Field of Classification Search
CPC ................................ C04B 28/02; C04B 28/04
See application file for complete search history.

(56) References Cited

U.S. PATENT DOCUMENTS

| | | | | | |
|---|---|---|---|---|---|
| 2,650,171 | A | * | 8/1953 | Schaaf | C04B 20/12 106/417 |
| 3,226,242 | A | * | 12/1965 | Huettemann | C04B 28/18 106/723 |
| 4,188,230 | A | * | 2/1980 | Gillott | C04B 28/36 501/140 |
| 5,741,357 | A | * | 4/1998 | Sheikh | C04B 20/1088 106/692 |
| 2014/0130620 | A1 | | 5/2014 | Tian et al. | |

FOREIGN PATENT DOCUMENTS

| | | |
|---|---|---|
| CN | 102866043 A | 1/2013 |
| CN | 103983489 A | 8/2014 |
| CN | 104034563 A | 9/2014 |
| CN | 104632204 A | 5/2015 |
| CN | 105842026 A | 8/2016 |

OTHER PUBLICATIONS

Jia Hu et al., Research on Physical Simulation Experiment Method of Fracture-cave Oil and Gas Reservoir, 2010, vol. 38 No. 6.
Tengqi, Crack Ultra-low Permeability Reservoir Physical Simulation Experiment Method and Application, University of Chinese Academy of Sciences, May 2014.
Tianfang Gao, Research on Ultra-low Permeability Reservoir Plane Physical Simulation Method, University of Chinese Academy of Sciences, May 2014.

* cited by examiner

*Primary Examiner* — Anthony Calandra
*Assistant Examiner* — Eric T Chen
(74) *Attorney, Agent, or Firm* — Gokalp Bayramoglu

(57) ABSTRACT

A manufacturing method of a big-model low-permeability microcrack core includes: (1) determining the size of a microcrack core to be manufactured; (2) placing stones in a baking oven to bake for 24h under 120° C., placing the stones into a mixer, mixing and spraying oil, enabling the oil to seep into the stone, evenly forming a thin oil film on stone's surface; (3) mixing the oil sprayed stone with quartz sand and cement, adding water to mix evenly to obtain cement paste; (4) spreading butter on core mold's inner surface to form a thin butter film, pouring the cement paste into the core mold to obtain a cement sample; (5) loading confining pressure outside the core according to the requirements of porosity and permeability of the mold to adjust a pore permeability value; (6) obtaining the big-model core with microcrack after the cement sample is dried and formed.

7 Claims, No Drawings

MANUFACTURING METHOD OF BIG-MODEL LOW-PERMEABILITY MICROCRACK CORE

CROSS REFERENCE TO RELATED APPLICATIONS

This application is the national phase entry of International Application No. PCT/CN2017/073489, filed on Feb. 14, 2017, which is based upon and claims priority to Chinese Patent Application No. 201710065729.0, filed on Feb. 6, 2017, the entire contents of which are incorporated herein by reference.

TECHNICAL FIELD

The present invention relates to a manufacturing method of a big-model low-permeability microcrack core in indoor simulation experiments of petroleum exploration and development.

BACKGROUND OF THE INVENTION

Low-permeability reservoir stratums are generally developed with microcracks, and the microcracks can be communicated with a relatively large seepage channel in the substrate hole and reservoir stratum, and improve the permeability of the substrate. It plays an important role improving the flow condition of fluid in stratum and increasing the production of an oil well. Physical simulation is an important means of stimulating the development of oil and gas reservoir. Practice shows that the larger the physical dimension of the model is, the more practical the experimental result to the oil field is. Experimental cores include a natural core and a man-made core, and since it is difficult to obtain the core with a microcrack that is easy to be broken, the man-made core is generally used in the experiment. Since the size of a drilling well to take the core is limited, the man-made core is more required to the large model. While the main focus is on the manufacturing of macrocracks, there is little research done in the manufacturing of microcracks, which a man-made method is usually used. For example, Chinese Invention Patent (201410260860.9) discloses a manufacturing method of a man-made core of a jointing shale, and provides that edible oatmeal with diameter of 5 to 8 mm is used in the cement sample to stimulate the microcrack, and the pattern of the stimulated microcrack is relatively simplex; Chinese Invention Patent (201510004960.X) discloses a manufacturing method of a hard brittle shale microcrack and a test system of sealing capacity, a shale crack maker is used to make the core crack, the dedusting and sculpture are conducted to the crack surface, half of it is stacked with a sluggish strip material with width of 2 mm and different thickness along edges of two longitudinal side, which stimulates the microcrack with different width ranging from 10 to 100 um, but the core used is standard core column with diameter of 25 mm and length of 30 mm.

Some scholars put forward that a uniform splitting method can stimulate the natural microcrack (Jia Hu, et al., Research on Physical Simulation Experiment Method of Fracture-cave Oil and Gas Reservoir, Vol. 38 No. 6, 2010), but this method needs to cut the core into two equal parts, the crack surface is relatively straight and smooth, and does not comply with the actual pattern of the microcrack, and it is difficult to manufacture multiple microcracks.

In 2014, Gao Tianfang from Chinese Academy of Sciences put forward in his master's thesis "Research on Ultra-low Permeability Reservoir Plane Physical Simulation Method" that the crack was cut by a sand wire, the width of the crack was controlled through adjusting the thickness of the sand wire, but there was a condition that the pattern of the crack surface did not comply with the actual pattern.

In 2014, Teng Qi from Chinese Academy of Sciences manufactured the microcrack by a method of conducting triaxial compression to one-dimensional core in his doctoral thesis "Crack Ultra-low Permeability Reservoir Physical Simulation Experiment Method and Application". This method was possible to form multiple cracks, but this method used many devices in generating cracks. The pressure used in generating crack was large, and the operation method was relatively complicated.

The stone can generate microcrack by a heating method, and the method is a traditional heating method and a microwave heating method. The heating is uneven by the traditional heating method and the transmission of the heat energy is relatively slow, and the microwave heating method can generate the problem of radiation security if it is improperly used.

SUMMARY OF THE INVENTION

The object of the present invention lies in providing a manufacturing method of a big-model low-permeability microcrack core, and the method uses simple materials, has low cost, and is simple and convenient to operate. The method can form microcracks with various patterns distributed randomly in the big-model cores, and can better stimulate the development process of a microcrack reservoir stratum.

In order to achieve the technical object above, the present invention provides the following technical solution.

A manufacturing method of a big-model low-permeability microcrack core comprises the following steps successively:

(1) determining the size of a microcrack core to be manufactured;
(2) placing stones in a baking oven to bake for 24 h under 120° C., placing the stones into a mixer, mixing and spraying oil, and placing for 2 h after mixing evenly to enable the oil to seep into the stone and evenly form a layer of thin oil film on the surface of the stones;
(3) mixing the stones sprayed by oil in step (2) with quartz sand and cement, and then adding water to mix evenly to obtain cement paste;
(4) spreading butter on the inner surface of a core mould to form a layer of thin butter film on the inner surface of the core mould, pouring the cement paste in step (3) into the core mould, and vibrating the cement paste in the core mould by a vibrating spear during pouring to obtain a cement sample;
(5) loading confining pressure outside the core according to the requirements on the degree of porosity of the mould and the permeability after pouring, so as to adjust a pore permeability value; and
(6) obtaining the large-scale core with microcrack after the cement sample is dried and formed.

In step (2), the stones are riverway stones with a diameter of 5 to 10 mm, which simulate conglomerate rock or the core developed with microcrack.

In step (3), the particle size of the quartz sand is 80 to 120 meshes, and the cement is ordinary portland cement.

In step (3), the mass ratio of the water to the cement is 0.3 to 0.6, the mass ratio of the cement to the quartz sand is 0.2 to 0.7, and the mass ratio of the stone to the quartz sand is 1.5 to 3.3.

In the present invention, the microcrack prevents the stones from bonding to the stones, the quartz sand and the cement through spraying a layer of oil on the surface of the stones.

Compared with the prior art, the present invention has the following beneficial effects.

(1) The present invention provides the method of establishing microcracks with various patterns in the cement cores;

(2) The present invention can control a pore permeability parameter through adjusting the ratio of the cement, the quartz sand, the water and the stones, and loading the confining pressure; and (3) The present invention can better stimulate carbonate rocks or sandstones with the microcracks, the materials are easy to be obtained, and the present invention has low cost and is simple and convenient to operate.

DETAILED DESCRIPTION OF THE INVENTION

The invention is further described with reference to the embodiments.

Embodiment 1

A manufacturing method of a big-model low-permeability microcrack core comprises the following steps successively.

(1) The size of a microcrack core to be manufactured is 30 cm×30 cm×30 cm.

(2) Stones are placed in a baking oven to bake for 24 h under 120° C., engine oil is sprayed on the surface, and the stones are placed for a period to wait the engine oil to seep into the stones and evenly form a layer of thin oil film on the surface of the stones. In the embodiment, the diameter of the stone is 10 mm.

(3) The stones sprayed by oil in step (2) are mixed with quartz sand and cement, and then water is added to mix evenly to obtain cement paste. The particle size of the quartz sand is 80 meshes, the cement is ordinary portland cement, the mass ratio of the water to the cement is 0.6, the mass ratio of the cement to the quartz sand is 0.5, and the mass ratio of the stone to the quartz sand is 2.

(4) Butter is spread on the inner surface of a core mould to form a layer of thin butter film on the inner surface of the core mould, the mixture in step (3) is poured into the core mould, and the cement paste in the core mould is vibrated by a vibrating spear during pouring to obtain a cement sample.

(5) 20 MPa confining pressure is loaded outside the core according to the requirements on the degree of porosity of the mould and the permeability after pouring the cores.

(6) The microcrack prevents the stones from bonding to the stones, quartz sand and cement through spraying a layer of oil on the surface of the stones. The big-model core with microcrack can be obtained after the cement sample is dried and formed. The degree of porosity of the cores is 10.66% and the permeability is 0.108 mD. The big-model cores manufactured according to the present invention have the microcracks with various patterns distributed randomly, have a certain degree of porosity and permeability, and can better stimulate low-permeability carbonate rock and sandstone reservoir stratum actually developed by the microcrack.

What is claimed is:

1. A manufacturing method of a big-model low-permeability microcrack core, comprising the following steps successively:
   (1) determining a size of a microcrack core to be manufactured;
   (2) placing a plurality of stones in a baking oven to bake for 24 h under 120° C., after baking, placing the plurality of stones into a mixer, mixing and spraying an oil, and keeping the mixture of the plurality of stones and the oil for 2 h after mixing evenly to enable the oil to seep into the plurality of stones and evenly forming a layer of thin oil film on a surface of the plurality of stones;
   (3) mixing the plurality of stones sprayed by the oil in step (2) with a quartz sand and a cement, and then adding water and mixing evenly to obtain a cement paste;
   (4) spreading a butter on an inner surface of a core mould to form a layer of thin butter film on the inner surface of the core mould, pouring the cement paste in step (3) into the core mould, and vibrating the cement paste in the core mould by a vibrating rod during pouring to obtain a cement sample;
   (5) loading a predetermined confining pressure outside the core according to a degree of porosity of the mould and the permeability after pouring, so as to adjust a pore permeability value; and
   (6) forming the big-model low-permeability microcrack core after drying the cement sample.

2. The manufacturing method of a big-model low-permeability microcrack core according to claim 1, wherein, in step (2), the plurality of stones are stones with a diameter of 5 to 10 mm, which simulate a conglomerate rock or a core developed with microcrack.

3. The manufacturing method of a big-model low-permeability microcrack core according to claim 1, wherein, in step (3), a particle size of the quartz sand is 80 to 120 meshes, and the cement is portland cement.

4. The manufacturing method of a big-model low-permeability microcrack core according to claim 1, wherein, in step (3), a mass ratio of the water to the cement is 0.3 to 0.6, a mass ratio of the cement to the quartz sand is 0.2 to 0.7, and a mass ratio of the stone to the quartz sand is 1.5 to 3.3.

5. The manufacturing method of a big-model low-permeability microcrack core according to claim 2, wherein, in step (3), a mass ratio of the water to the cement is 0.3 to 0.6, a mass ratio of the cement to the quartz sand is 0.2 to 0.7, and a mass ratio of the stone to the quartz sand is 1.5 to 3.3.

6. The manufacturing method of a big-model low-permeability microcrack core according to claim 3, wherein, in step (3), a mass ratio of the water to the cement is 0.3 to 0.6, a mass ratio of the cement to the quartz sand is 0.2 to 0.7, and a mass ratio of the stone to the quartz sand is 1.5 to 3.3.

7. The manufacturing method of a big-model low-permeability microcrack core according to claim 3, wherein, the predetermined confining pressure is 20 MPa, the degree of porosity of the mould is 10.66% and the pore permeability value is 0.108mD.

* * * * *